United States Patent
Griffiths et al.

(10) Patent No.: US 7,417,153 B2
(45) Date of Patent: Aug. 26, 2008

(54) METHOD FOR THE PRODUCTION OF 3-AMINO-5-(HYDROXYMETHYL) CYCLOPENTANE-1,2-DIOL DERIVATIVES

(75) Inventors: Gareth-John Griffiths, Visp (CH); Silvia Lange, Brig (CH); Walter Brieden, Ausserberg (CH)

(73) Assignee: Lonza AG, Basel (CH)

( * ) Notice: Subject to any disclaimer, the term of this patent is extended or adjusted under 35 U.S.C. 154(b) by 116 days.

(21) Appl. No.: 10/584,848

(22) PCT Filed: Jan. 24, 2005

(86) PCT No.: PCT/EP2005/000643

§ 371 (c)(1),
(2), (4) Date: Aug. 15, 2006

(87) PCT Pub. No.: WO2005/073213

PCT Pub. Date: Aug. 11, 2005

(65) Prior Publication Data

US 2007/0043225 A1   Feb. 22, 2007

(30) Foreign Application Priority Data

Jan. 30, 2004   (EP)   ................... 04002055

(51) Int. Cl.
*C07D 209/52* (2006.01)
*C07D 209/54* (2006.01)
*C07D 209/56* (2006.01)
*C07D 209/96* (2006.01)
*C07D 317/44* (2006.01)

(52) U.S. Cl. ............... 548/407; 548/421; 548/452; 549/336; 549/439

(58) Field of Classification Search ............... 549/336, 549/439; 548/407, 421, 452
See application file for complete search history.

(56) References Cited

U.S. PATENT DOCUMENTS

| 5,364,864 | A | 11/1994 | Spada et al. |
| 5,631,383 | A | 5/1997 | Largeau et al. |
| 5,670,649 | A | 9/1997 | Largeau et al. |
| 5,684,159 | A | 11/1997 | O'Brien et al. |
| 5,808,093 | A | 9/1998 | O'Brien et al. |
| 5,831,096 | A | 11/1998 | Leon et al. |
| 5,886,192 | A | 3/1999 | Leon et al. |
| 6,376,472 | B1 | 4/2002 | Myers et al. |
| 6,780,634 | B1 | 8/2004 | Bernegger-Egli et al. |
| 2002/0099030 | A1 | 7/2002 | Myers et al. |
| 2003/0069423 | A1 | 4/2003 | Ayers et al. |
| 2004/0167351 | A1 | 8/2004 | Bernegger-Egli et al. |

FOREIGN PATENT DOCUMENTS

| WO | 95/28160 | 10/1995 |
| WO | 97/03053 | 1/1997 |
| WO | 98/01426 | 1/1998 |
| WO | 00/03032 | 1/2000 |
| WO | 00/23447 | 4/2002 |
| WO | 02/091988 | 11/2002 |

*Primary Examiner*—Bernard Dentz
(74) *Attorney, Agent, or Firm*—Fisher, Christen & Sabol

(57) ABSTRACT

A method for the production of acetals and ketals of 3-amino-5-(hydroxymethyl) cyclopenlane-1,2-diols of formula (I):

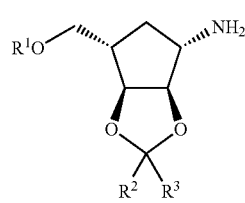

(and/or the enantiomer), where $R^1$ is H, $C_{1-6}$-alkyl, $C_{3-8}$-cycloalkyl or benzyl and (i) $R^2$ is methyl and $R^3$ is ethyl, (ii) $R^2$ is H and $R^3$ is $C_{1-6}$-alkyl or phenyl or (iii) $R^2$ and $R^3$ together form a group of formula —$(CH_2)_n$— with n=4 to 6, present as free amines or as salts of di- or tri-basic organic acids, starting from 2-acetyl-2-aza-bicyclo[2.2.1]hept-5-en-3-one of formula (II):

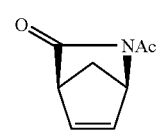

(and/or the enantiomer). The method is equally useful, depending on the starting material, for the production of enantiomerically-pure compounds, or mixtures with arbitrary enantiomeric content.

32 Claims, No Drawings

METHOD FOR THE PRODUCTION OF 3-AMINO-5-(HYDROXYMETHYL) CYCLOPENTANE-1,2-DIOL DERIVATIVES

This application is a 371 U.S. national stage application of International Application No. PCT/EP2005/000643, filed on Jan. 24, 2005, that has priority benefit of European Patent Application No. 04002055.4, filed on Jan. 30, 2004.

The invention relates to a method for preparing acetals and ketals of 3-amino-5-(hydroxymethyl)cyclopentane-1,2-diols, and their derivatives and salts of organic acids such as, for example, 2,3-isopropylidenedioxy-4-(methoxymethyl)cyclopentan-1-amine hydrogen oxalate, starting from 2-acetyl-2-azabicyclo[2.2.1]hept-5-en-3-one of the formula

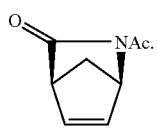

II and/or mirror image.

Enantiopure compounds mean hereinafter mixtures of enantiomers with an enantiomeric excess (ee) of at least 90%.

$C_{1-6}$-Alkyl means hereinafter a linear or branched aliphatic alkyl group having 1 to 6 carbon atoms, such as, for example, methyl, ethyl, propyl, isopropyl, n-butyl, isobutyl, sec-butyl, tert-butyl, pentyl, hexyl.

$C_{3-8}$-Cycloalkyl means hereinafter an alicyclic alkyl group having 3 to 8 carbon atoms, such as, for example, cyclopropyl, cyclobutyl, cyclopentyl, cyclohexyl, cycloheptyl or cyclooctyl.

Alcoholic solution or suspension means hereinafter a solution or suspension of at least one organic compound in any mixture of ethanol, methanol, propanol, isopropyl alcohol, n-butanol, isobutanol and/or tert-butanol, where appropriate mixed with water and/or further solvents, solubilizers or further auxiliaries.

The method is, irrespective of the composition of the precursor, equally suitable for preparing enantiopure compounds or mixtures of any composition of enantiomers. The enantiomer which is not depicted in each case is intended to be included in the depictions of the structural formulae by the addition of "and/or mirror image" or "or mirror image".

Substituted cyclopentylamines such as, for example, (1R,2S,3R,4R)-2,3-isopropylidenedioxy-4-(methoxymethyl)cyclopentan-1-amine hydrochloride are intermediates for preparing pharmaceutically active adenosine derivatives which can be employed inter alia for the treatment of coronary perfusion impairments, heart failure and high blood pressure (U.S. Pat. No. 5,364,862 and WO-A-95/28160).

In a known method for preparing (1R,2S,3R,4R)-2,3-isopropylidenedioxy-4-(methoxymethyl)cyclopentan-1-amine hydrochloride (WO-A-98/01426 and WO-A-00/23447), (−)-5,6-isopropylidenedioxy-2-azabicyclo[2.2.1]heptan-3-one is converted, using the very costly and hydrolysis-sensitive compound di-tert-butyl dicarbonate, into the correspondingly protected N—BOC derivative. Synthesis of the precursor (compound of the formula vi) starting from 5,6-dihydroxy-2-azabicyclo[2.2.1]heptan-3-one is disclosed in WO-A-95/28160. After lactam cleavage, where appropriate followed by a methylation of the newly produced hydroxyl group, the BOC protective group is eliminated using HCl gas. Hydrochlorides are obtained in this method, but their purity, yield or physicochemical properties are not specified. The substances obtained are employed without further workup directly in the respective next stages of the synthesis.

The method disclosed in the prior art for preparing (1R,2S,3R,4R)-2,3-isopropylidenedioxy-4-(methoxymethyl)cyclopentan-1-amine hydrochloride has disadvantages which prevent industrial implementation of the method. It was therefore an object of the present invention to provide an economic method which can be carried out industrially to prepare acetals and ketals of 3-amino-5-(hydroxymethyl)cyclopentane-1,2-diols, and their derivatives and salts of organic acids.

This object has been achieved in the method as claimed in claim 1 starting from 2-acetyl-2-azabicyclo[2.2.1]hept-5-en-3-one.

It is possible by the method of the invention to prepare inter alia enantiopure hydrogen oxalates of (1R,2S,3R,4R)-2,3-isopropylidenedioxy-4-(hydroxylmethyl)cyclopentan-1-amine and of (1R,2S,3R,4R)-2,3-isopropylidenedioxy-4-(methoxymethyl)cyclopentan-1-amine.

The method of the invention can be carried out with (−)-2-acetyl-2-azabicyclo[2.2.1]hept-5-en-3-one or (+)-2-acetyl-2-azabicyclo[2.2.1]hept-5-en-3-one, and any mixture thereof.

The compound 2-acetyl-2-azabicyclo[2.2.1]hept-5-en-3-one as mixture of enantiomers, and the enantiopure form (−)-2-acetyl-2-azabicyclo[2.2.1]hept-5-en-3-one, are disclosed in WO-A-00/03032.

The method makes do with conventional and low-cost protective group techniques through the use of acetylated lactams. Use of the acetyl protective group in the method of the invention is notable for simpler manipulation in particular by comparison with the BOC protective group used in the prior art.

It is further possible for the acetyl group easily to be removed again in an alkaline hydrolysis step, whereas the method of WO-A-98/01426 depends on the use of HCl gas to eliminate the BOC protective group. Compared with the method of WO-A-98/01426, in which considerable quantities of NaCl waste are produced and which requires a large expenditure to protect systems and lines from corrosion, the method of the invention represents a substantial advance.

It has been found that cyclic acetals and ketals of dihydroxycyclopentylamines of the formula

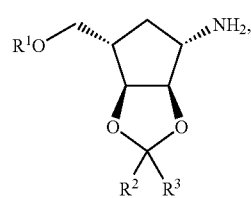

I and/or mirror image which are prepared by the method of the invention can advantageously be precipitated as hydrogen oxalates which exhibit substantial advantages in manipulation (filtration, centrifugation) compared with previously disclosed hydrochlorides.

The salts which can be prepared by the method of the invention, such as, (1R,2S,3R,4R)-2,3-isopropylidenedioxy-4-(methoxymethyl)-cyclopentan-1-amine hydrogen oxalate can in principle be obtained by anion exchange and reprecipitation from the corresponding hydrochlorides. However, they are not obtainable as direct hydrolysis product from the N—BOC compound mentioned in WO-A 00/23447, because the BOC protective group must first be eliminated with a strong acid. Moreover, reprecipitation of an HCl-acidic salt with an organic acid is not favored.

A method for preparing compounds of the formula

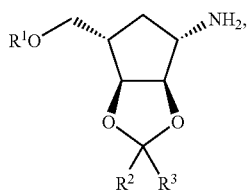

I and/or mirror image in which $R^1$ is hydrogen, $C_{1-6}$-alkyl, $C_{3-8}$-cycloalkyl or benzyl, and in which i) $R^2$ is methyl and $R^3$ is ethyl, ii) $R^2$ is hydrogen and $R^3$ is $C_{1-6}$-alkyl or phenyl or iii) $R^2$ and $R^3$ together are a group of the formula —$(CH_2)_n$— with n=4 to 6, and which are in the form of free amines or of salts of dibasic or tribasic organic acids, is described.

For this purpose, in a first reaction step, a 2-acetyl-2-azabicyclo[2.2.1]hept-5-en-3-one of the formula

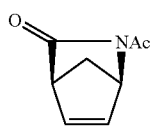

II and/or mirror image is converted by cis hydroxylation of the double bond into a 2-acetyl-5,6-dihydroxy-2-azabicyclo[2.2.1]-heptan-3-one of the formula

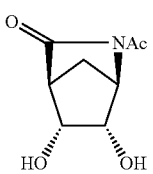

III and/or mirror image.

In a second reaction step, a compound of the formula III is converted by reaction with a ketone or an aldehyde of the formula $R^2$—CO—$R^3$ or by reaction with 2,2-dimethoxypropane or 2,2-dimethoxybutane into a ketal or acetal of the formula

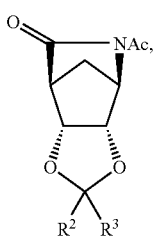

IV and/or mirror image in which $R^2$ and $R^3$ have the stated meanings.

In the following reaction step, a compound of the formula IV is converted by reductive ring opening into a compound of the formula

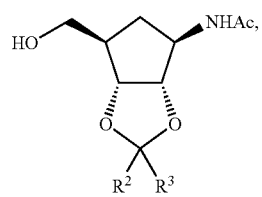

V and/or mirror image where $R^2$ and $R^3$ have the stated meanings.

In an optionally following reaction step, an alcohol of the formula V, or where appropriate an alcoholate thereof, where $R^2$ and $R^3$ have the stated meanings, is converted by reaction with an alkylating agent such as, for example, dimethyl sulfate (DMS), benzyl chloride or a halide of the formula $R^1$—X in which $R^1$ has the stated meaning apart from hydrogen, and X is bromine or iodine, into an ether of the formula

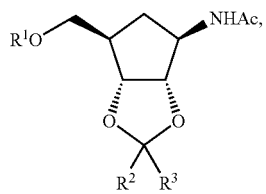

VI and/or mirror image where $R^2$ and $R^3$ have the stated meanings.

In a further reaction step, one of the compounds obtained in the two preceding reaction steps is converted by alkaline hydrolysis into a compound of the formula

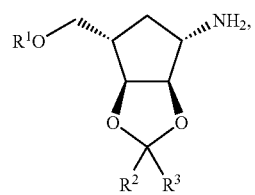

I and/or mirror image in which $R^1$, $R^2$ and $R^3$ have the stated meanings.

In an optionally following last reaction step, compounds of the formula I are reacted with a dibasic or tribasic organic acid to give the corresponding salts in which $R^1$, $R^2$ and $R^3$ have the stated meanings.

To increase the conversion and save on oxidizing agent before the cis hydroxylation, interfering compounds are removed from the synthesis of the 2-acetyl-2-azabicyclo[2.2.1]hept-5-en-3-one advantageously by extraction. The commonest impurity 4-dimethylaminopyridine (DMAP) can be removed for example by acid extraction with a dilute aqueous acid such as, for example, dilute HCl or $H_2SO_4$.

In a preferred embodiment, the cis hydroxylation of the double bond is carried out using an inorganic oxidizing agent such as, for example, osmium tetraoxide, potassium osmate or potassium permanganate.

Because of the toxicity and volatility of osmium tetraoxide, the hydroxylation is carried out in a further preferred embodiment with use of a 2 to 10% strength aqueous solution of osmium tetraoxide or with osmium tetraoxide immobilized on an organic or inorganic support.

In a particularly preferred embodiment, osmium tetraoxide is employed in an amount of from 0.1 to 2 mol % in relation to 2-acetyl-2-azabicyclo[2.2.1]hept-5-en-3-one, preferably in an amount of from 0.2 to 0.9 mol %.

The osmium tetraoxide can advantageously be regenerated during the reaction in the presence of at least one organic N-oxide such as, for example, N-4-methylmorpholine N-4-oxide, and/or of a secondary or tertiary amine and at least one inorganic oxidizing agent such as, for example, hydrogen peroxide. Suitable as co-oxidant for regenerating osmium tetraoxide during the reaction are sterically demanding N-oxides such as N-4-methylmorpholine N-4-oxide, di- and tri-alkylamine N-oxides such as trimethylamine N-oxide, or mixtures of said secondary and tertiary amines with organic or inorganic oxidizing agents such as, for example, tert-butyl hydroperoxide, magnesium monoperoxyphthalate, 3-chloroperbenzoic acid, hydrogen peroxide, sodium and/or potassium perchlorate, periodate or permanganate. The use of N-oxides and mixtures of said amines with hydrogen peroxide is particularly preferred.

In a particularly preferred method, enantiopure (−)-2-acetyl-2-azabicyclo[2.2.1]hept-5-en-3-one is converted by cis hydroxylation with osmium tetraoxide into (1R,4S,5R,6S)-2-acetyl-5,6-dihydroxy-2-azabicyclo-[2.2.1]heptan-3-one of the formula

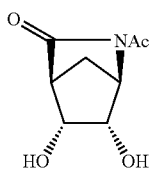

III

In a preferred variant of the method, the acetal or ketal formation is carried out with acid catalysis.

In a particularly preferred variant of the method, sulfuric acid and/or p-toluenesulfonic acid is used for the acid catalysis.

In a preferred method, 2-acetyl-5,6-dihydroxy-2-azabicyclo[2.2.1]heptan-3-one of the formula III is converted by reaction with acetone or 2,2-dimethoxypropane into 8-acetyl-4,4-dimethyl-3,5-dioxa-8-azatricyclo[5.2.1.0$^{2,6}$]decan-9-one of the formula

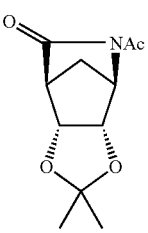

IVa and/or mirror image.

In a particularly preferred variant of the method, (1R,4S,5R,6S)-2-acetyl-5,6-dihydroxy-2-azabicyclo[2.2.1]heptan-3-one is converted by reaction with acetone or 2,2-dimethoxypropane into (1S,2R,6S,7R)-8-acetyl-4,4-dimethyl-3,5-dioxa-8-azatricyclo[5.2.1.0$^{2,6}$]-decan-9-one (IVa).

In a preferred method, the reductive ring opening is carried out with a complex metal hydride such as, for example, LiBH$_4$, NaBH$_4$, NaAlH$_2$(OCH$_2$CH$_2$OCH$_3$)$_2$ or LiAlH$_4$, preferably with NaBH$_4$.

In a further preferred method, (1S,2R,6S,7R)-8-acetyl-4,4-dimethyl-3,5-dioxa-8-azatricyclo[5.2.1.0$^{2,6}$]decan-9-one is converted by reaction with a complex metal hydride into (1R,2S,3R,4R)-N-[2,3-isopropylidenedioxy-4-(hydroxymethyl)cyclopentan-1-yl]acetamide of the formula:

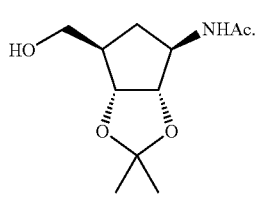

Va

In a preferred variant of the method, the formation of the ether of the formula VI with R$^1$ methyl is carried out with DMS in acetone, in the presence of a strong base such as, for example, NaOH and/or KOH, particularly preferably with a water content of less than 1% based on the solvent.

In a further preferred variant of the method, the ether formation is carried out with a C$_{1-6}$-alkyl or C$_{3-8}$-cycloalkyl halide in the presence of AgOH.

In a particularly preferred method, (1R,2S,3R,4R)-N-[2,3-isopropylidenedioxy-4-(hydroxymethyl)cyclopentan-1-yl]acetamide is converted by reaction with DMS or methyl iodide into (1R,2S,3R,4R)-N-[2,3-isopropylidenedioxy-4-(methoxymethyl)cyclopentan-1-yl]acetamide

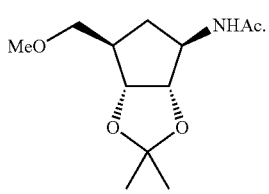

VIa

In a preferred variant of the method, the alkaline hydrolysis is carried out with at least one alkali metal or alkaline earth metal hydroxide selected from the group consisting of LiOH, NaOH, KOH, Mg(OH)$_2$, Ca(OH)$_2$ and Ba(OH)$_2$, in aqueous and/or alcoholic solution or suspension.

In a preferred variant of the method, the alkaline hydrolysis is carried out under a pressure of from 1 to 10 bar, particularly preferably from 1 to 2 bar, and at temperatures of from 50 to 150° C., particularly preferably from 80 to 100° C.

In a particularly preferred variant of the method, the alkaline hydrolysis is carried out with NaOH and/or KOH in methanolic and/or ethanolic solution under a pressure of from 1 to 2 bar and at a temperature of from 80 to 100° C.

In a preferred method, alkaline hydrolysis with NaOH and/or KOH in methanolic and/or ethanolic solution, preferably under a pressure of from 1 to 2 bar and temperatures of from 80 to 100° C., converts i) (1R,2S,3R,4R)-N-[2,3-isopropylidenedioxy-4-(hydroxymethyl)cyclopentan-1-yl]acetamide into (1R,2S,3R,4R)-2,3-isopropylidenedioxy-4-(hydroxylmethyl)cyclopentane-1-amine or

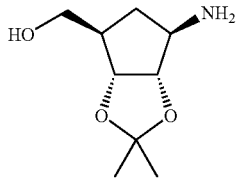

Ia ii) (1R,2S,3R,4R)-N-[2,3-isopropylidenedioxy-4-(methoxymethyl)cyclopentan-1-yl]acetamide into (1R,2S,3R,4R)-2,3-isopropylidenedioxy-4-(methoxymethyl)cyclopentane-1-amine

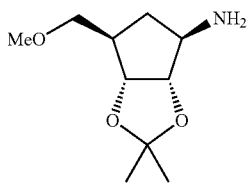

Ib

In a preferred variant of the method, the salt formation in the optional last reaction step is carried out with an organic acid selected from the group consisting of oxalic acid free of water of crystallization or containing water of crystallization, (+)-, (−)- or meso-tartaric acid, (+)- or (−)-malic acid, tartronic acid, mesoxalic acid and oxaloacetic acid.

In a particularly preferred variant of the method, the salt formation is carried out with oxalic acid free of water of crystallization or containing water of crystallization, (+)-, (−)- or meso-tartaric acid, (+)- or (−)-malic acid.

In a further particularly preferred variant of the method, the compounds (1R,2S,3R,4R)-2,3-isopropylidenedioxy-4-(hydroxymethyl)cyclopentan-1-amine or (1R,2S,3R,4R)-2,3-isopropylidenedioxy-4-(methoxymethyl)cyclopentan-1-amine are converted into the corresponding hydrogen oxalates.

The invention also relates to compounds of the formula

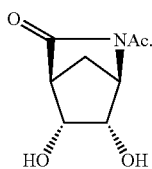

III or mirror image.

Likewise encompassed by the invention are compounds of the formula

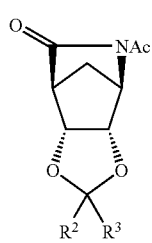

IV or mirror image in which $R^2$ and $R^3$ have the abovementioned meanings.

Further encompassed by the invention are compounds of the formula

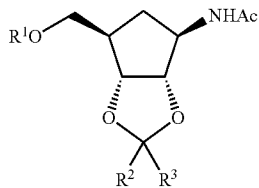

VI or mirror image in which $R^1$ has the stated meaning including hydrogen, and $R^2$ and $R^3$ have the abovementioned meanings. Additionally encompassed by the invention are salts of dibasic and tribasic organic acids of compounds of the formula

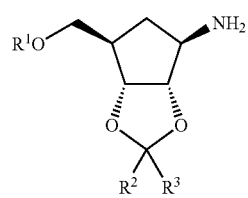

I or mirror image in which $R^1$, $R^2$ and $R^3$ have the abovementioned meanings.

EXAMPLES

Although the present invention is completely disclosed by the quoted Examples 1 to 18 of the invention, numerous further examples of the invention can also be carried out because of the claimed variations in the parameters of the method. Examples carried out by implementing these variations which are defined in the description and in the claims are intended to be regarded as examples of the invention and fall within the range of protection of this patent application.

Example 1

(1R,4S,5R,6S)-2-Acetyl-5,6-dihydroxy-2-azabicyclo-[2.2.1]heptan-3-one (formula III)

132.1 g (0.87 mol) of (−)-2-acetyl-2-azabicyclo[2.2.1]hept-5-en-3-one and 118.1 g (0.87 mol) of N-4-methylmorpholine N-4-oxide.H$_2$O were introduced into 750 ml of acetone, 224 ml of deionized water and 75 ml of tert-butanol. The reaction solution was warmed to 30° C. A solution of 2.0 g (7.9 mmol) of osmium tetraoxide in 10 ml of acetone was added dropwise over the course of 15 minutes, and the reaction mixture was stirred at 30° C. for 2 hours. The reaction solution was then cooled to 10° C. and, to reduce excess N-4-methylmorpholine N-4-oxide and osmium tetraoxide, 180.1 g (0.69 mol) of 40% strength sodium bisulfite solution were added over a period of 1 hour. The reaction mixture was then adjusted to pH 7 with 35.1 g of conc. sulfuric acid. The resulting suspension was filtered and the material on the filter was washed with 20 ml of acetone. The filtrate was concentrated in vacuo (40 to 400 mbar) at a temperature of 40° C. to 350 to 400 ml. The reaction solution was cooled to 20° C. The aqueous phase was adjusted to pH 2 with 12.9 g of conc. sulfuric acid and, after separation, extracted with ethyl acetate (5×400 ml). The combined organic phases were evaporated to dryness. The resulting residue was dried under high vacuum overnight.

Yield: 81.6 g (0.44 mol) of (1R,4S,5R,6S)-2-acetyl-5,6-dihydroxy-2-azabicyclo[2.2.1]heptan-3-one, approx. 50% based on (−)-2-acetyl-2-azabicyclo[2.2.1]hept-5-en-3-one.

$^1$H-NMR (300 MHz) in $CDCl_3$: δ 4.89 (2H, s (broad); 4.57 (1H, m); 4.17 (1H, m); 4.01 (1H, m); 2.83 (1H, m); 2.39 (3H, s); 2.14 (1H, m); 1.92 (1H, m).

Example 2

(1S,2R,6S,7R)-8-Acetyl-4,4-dimethyl-3,5-dioxa-8-azatricyclo[5.2.1.0$^{2,6}$]decan-9-one (formula IVa=formula IV with $R^2=R^3$=methyl)

72.2 g (0.39 mol) of (1R,4S,5R,6S)-2-acetyl-5,6-dihydroxy-2-azabicyclo[2.2.1]heptan-3-one, 49.8 g (0.47 mmol) of 2,2-dimethoxypropane and 1.48 g (7.8 mmol) of p-toluenesulfonic acid were introduced into 145 ml of ethanol. The clear brown solution was heated to 50° C., stirred at 50° C. for 2 hours, cooled to 0° C. over the course of 30 minutes and then mixed with 50 ml of ethanol. The brown suspension was stirred at 0° C. for 1 hour. The crystals which had separated out were filtered off and washed with 25 ml of ethanol. The moist product was dried in vacuo at 40° C.

Yield: 53.0 g (0.24 mol) of (1S,2R,6S,7R)-8-acetyl-4,4-dimethyl-3,5-dioxa-8-azatricyclo[5.2.1.0$^{2,6}$]decan-9-one, approx. 56% based on (1R,4S,5R,6S)-2-acetyl-5,6-dihydroxy-2-azabicyclo[2.2.1]heptan-3-one.

$^1$H-NMR (300 MHz) in $CDCl_3$: δ 4.74 (1H, m); 4.56 (1H, m); 4.43 (1H, m); 2.94 (1H, m); 2.41 (3H, s); 2.16 (1H, m); 1.95 (1H, m); 1.49 (3H, s); 1.34 (3H, s).

Example 3

(1R,2S,3R,4R)-N-[2,3-Isopropylidenedioxy-4-(hydroxymethyl)-cyclopentan-1-yl]acetamide (formula Va =formula V with $R^2=R^3$=methyl)

18.0 g (0.08 mol) of (1S,2R,6S,7R)-8-acetyl-4,4-dimethyl-3,5-dioxa-8-azatricyclo[5.2.1.0$^{2,6}$]decan-9-one were introduced into 250 ml of methanol, and the clear colorless solution was cooled to 0° C. Over the course of 1 hour, 6.6 g (0.17 mol) of sodium borohydride were added in portions in such a way that the temperature was kept below 5° C.

The reaction mixture was then warmed to 20° C. over the course of 30 minutes and stirred at 20° C. for 15 hours. Subsequently, 17.5 g of acetic acid were added dropwise over the course of 10 minutes, and the reaction mixture was stirred for a further 10 minutes and then evaporated to dryness. The residue (44.8 g) was taken up in 100 ml of ethyl acetate and stirred for about 10 minutes. The crystals which separated out were filtered off and washed with ethyl acetate (2×20 ml). The filtrate was evaporated and dried under high vacuum. The crude product (21.3 g) was purified by column chromatography on silica gel (mobile phase ethyl acetate/methanol (5:1)).

Yield: 18.4 g (0.08 mmol) of (1R,2S,3R,4R)-N-[2,3-isopropylidenedioxy-4-(hydroxymethyl)cyclopentan-1-yl]acetamide, approx. 100% based on [1S,2R,6S,7R]-8-acetyl-4,4-dimethyl-3,5-dioxa-8-azatricyclo[5.2.1.0$^{2,6}$]decan-9-one.

$^1$H-NMR (300 MHz) in $CDCl_3$: δ 7.51 (1H, d); 4.60 (1H, m) 4.37 (1H, m); 4.34 (1H, m); 4.0 (1H, s, broad); 3.86 (1H, dd); 3.67 (1H, dd); 2.52 (1H, m); 2.33 (1H, m); 1.94 (3H, s); 1.49 (1H, m); 1.46 (3H, s); 1.28 (3H, s).

Example 4

(1R,2S,3R,4R)-N-[2,3-Isopropylidenedioxy-4-(methoxymethyl)cyclopentan-1-yl]acetamide (formula IVa=formula IV with $R^1=R^2=R^3$=methyl)

31.2 g (0.14 mol) of (1R,2S,3R,4R)-N-[2,3-isopropylidenedioxy-4-(hydroxymethyl)cyclopentan-1-yl]acetamide and 5.4 g of sodium hydroxide solution (40% strength) were introduced into 250 ml of acetone and heated to 50° C. In parallel, 20.2 g (0.16 mol) of dimethyl sulfate and 5.7 g of sodium hydroxide solution (40% strength) were added dropwise at 5° C. over the course of 90 minutes. The reaction mixture was stirred at 50° C. for a further 3 hours and then concentrated in vacuo to a volume of about 90 ml. The residue was mixed with 54 ml of water and 100 ml of ethyl acetate and stirred for 30 minutes. The phases were separated and the aqueous phase was extracted with ethyl acetate (2×70 ml). The combined organic phases were evaporated to dryness.

The crude product (31.5 g) was purified by distillation (boiling point 120 to 130° C. under 0.15 mbar).

Yield: 16.9 g (0.07 mol) of (1R,2S,3R,4R)-N-[2,3-isopropylidenedioxy-4-(methoxymethyl)cyclopentan-1-yl]acetamide, approx. 51% based on (1R,2S,3R,4R)-N-[2,3-isopropylidenedioxy-4-(hydroxymethyl)cyclopentan-1-yl]-acetamide.

$^1$H-NMR (300 MHz) in $CDCl_3$: δ 6.83 (1H, d); 4.52 (1H, m); 4.37 (1H, m); 4.34 (1H, m); 3.55 (1H, dd); 3.42 (1H, dd); 3.41 (3H, s); 2.53 (1H, m); 2.34 (1H, m); 1.93 (3H, s); 1.45 (3H, s); 1.42 (1H, m); 1.27 (3H, s).

Example 5

(1R,2S,3R,4R)-2,3-Isopropylidenedioxy-4-(methoxymethyl)cyclopentan-1-amine (formula Ia=formula I with $R^1=R^2=R^3$=methyl)

A suspension of 2.34 g (0.01 mol) of (1R,2S,3R,4R)-N-[2,3-isopropylidenedioxy-4-(methoxymethyl)cyclopentan-1-yl]acetamide and 1.5 ml of $Ba(OH)_2.H_2O$ (30% strength suspension in water) in 1.2 ml of water was stirred under reflux at 100° C. for 22 hours. The suspension was cooled to 20° C., mixed with 50 ml of toluene and filtered. The phases were separated and the aqueous phase was extracted with toluene (2×50 ml). The combined organic phases were evaporated to dryness.

Yield: 1.5 g (7.5 mmol) of (1R,2S,3R,4R)-2,3-isopropylidenedioxy-4-(methoxymethyl)cyclopentan-1-amine as yellow liquid, approx. 75% based on (1R,2S,3R,4R)-N-[2,3-isopropylidenedioxy-4-(methoxymethyl)cyclopentan-1-yl]acetamide.

$^1$H-NMR (300 MHz) in $CDCl_3$: δ 4.48 (1H, dd); 4.19 (1H, dd); 3.43 (2H, d); 3.37 (1H, m); 3.36 (3H, s); 2.30 (1H, m); 2.24 (1H, m); 1.47 (3H, s); 1.43 (2H, s, broad); 1.33 (1H, m); 1.29 (3H, s).

Example 6

(1R,2S,3R,4R)-2,3-Isopropylidenedioxy-4-(methoxymethyl)cyclopentan-1-amine hydrogen oxalate (salt of the compound of the formula I with $R^1=R^2=R^3$=methyl)

17.0 g of anhydrous oxalic acid (0.19 mol) were added in portions to a solution of 42.1 g (0.21 mol) of (1R,2S,3R,4R)-2,3-isopropylidenedioxy-4-(methoxymethyl)cyclopentan-1-amine in 107 ml of ethanol at 25° C. The reaction solution was stirred at 25° C. for 30 minutes. Then 430 ml of acetone and 55 ml of heptane were successively added, followed by cooling to 0° C. and stirring at 0° C. for a further 60 minutes. The crystals which separated out were filtered off and washed with 110 ml of heptane. The residue on the filter was dried in vacuo at 40° C.

Yield: 42.7 g (0.15 mol) of (1R,2S,3R,4R)-2,3-isopropylidenedioxy-4-(methoxymethyl)cyclopentan-1-amine hydrogen oxalate, approx. 70% based on (1R,2S,3R,4R)-2,3-isopropylidenedioxy-4-(methoxymethyl)cyclopentan-1-amine.

$^1$H-NMR (300 MHz) in DMSO-d$_6$: δ 8.73 (4H, s, broad); 4.50 (1H, m); 4.40 (1H, m); 3.36 (3H, m); 3.27 (3H, s); 2.23 (2H, m); 1.57 (1H, m); 1.42 (3H, s); 1.23 (3H, s).

Example 7

(1R,2S,3R,4R)-2,3-Isopropylidenedioxy-4-(hydroxymethyl)cyclopentan-1-amine (formula Ia=formula I with R$^1$=H, R$^2$=R$^3$=methyl)

A solution of 3.5 g (15.3 mmol) of (1R,2S,3R,4R)-N-[2,3-isopropylidenedioxy-4-(hydroxymethyl)cyclopentan-1-yl] acetamide in 25 ml of ethanol and 7.8 g of 50% strength sodium hydroxide solution were heated in an autoclave at 100° C. and 2 bar for 15.5 hours. The reaction mixture was cooled to room temperature. The orange suspension was then dissolved in 30 ml of ethanol and evaporated to dryness in vacuo. The residue was mixed with 10 ml of water and evaporated to dryness in vacuo. The residue was then extracted with methyl tert-butyl ether (MTBE) (2×10 ml), and the combined organic phases were evaporated to dryness in vacuo.

Yield: 2.2 g (11.7 mmol) of (1R,2S,3R,4R)-2,3-isopropylidenedioxy-4-(hydroxymethyl)cyclopentan-1-amine, approx. 76% based on (1R,2S,3R,4R)-N-[2,3-isopropylidenedioxy-4-(hydroxymethyl)cyclopentan-1-yl]acetamide.

$^1$H-NMR (300 MHz) in CDCl$_3$: δ 4.78 (1H, d); 4.22, (1H, d); 3.72 (1H, dd); 3.55 (1H, dd); 3.53 (1H, m); 2.44 (2H, m); 1.44 (3H, s); 1.30 (1H, m); 1.29 (3H, s).

Example 8

(1R,2S,3R,4R)-2,3-Isopropylidenedioxy-4-(hydroxymethyl)cyclopentan-1-amine hydrogen oxalate (salt of the compound of the formula I with R$^1$=H, R$^2$=R$^3$=methyl)

0.48 g (5.3 mmol) of oxalic acid and ethanol (2×3 ml) were added in portions to a stirred solution of 1.0 g (5.3 mmol) of (1R,2S,3R,4R)-2,3-isopropylidenedioxy-4-(hydroxymethyl)cyclopentan-1-amine in 3 ml of ethanol. The white precipitate was filtered off and dried in vacuo at room temperature.

Yield: 1.0 g (3.7 mmol) of (1R,2S,3R,4R)-2,3-isopropylidenedioxy-4-(hydroxymethyl)cyclopentan-1-amine hydrogen oxalate, approx. 70% based on (1R,2S,3R,4R)-2,3-isopropylidenedioxy-4-(hydroxymethyl)cyclopentan-1-amine.

$^1$H-NMR (300 MHz) in DMSO-d$_6$: δ 6.95 (5H, s, broad); 4.46 (2H, m); 3.52 (1H, dd); 3.20 (2H, m); 2.26 (1H, m); 2.17 (1H, m); 1.57 (1H, m); 1.40 (3H, s); 1.23 (3H, s).

Example 9

(1SR,2RS,6SR,7RS)-8-Acetyl-4,4-dimethyl-3,5-dioxa-8-azatricyclo[5.2.1.0$^{2,6}$]decan-9-one (formula IVa=formula IV with R$^2$=R$^3$=methyl)

A mixture of 72.2 g (0.39 mol) of (1SR,4SR,5RS,6SR)-2-acetyl-5,6-dihydroxy-2-azabicyclo[2.2.1]heptan-3-one, 49.8 h (0.47 mol) of 2,2-dimethoxypropane and 1.48 g (7.8 mmol) of 4-toluenesulfonic acid monohydrate in 145 ml of ethanol was heated at 50° C. for 90 min. The reaction mixture was then cooled to 0° C. over the course of 30 minutes and stirred for a further 75 minutes. The crystals which separated out were filtered off, washed with 25 ml of ethanol and dried at 40° C. and 30 mbar.

Yield: 53.0 g (0.24 mol) of (1SR,2RS,6SR,7RS)-8-acetyl-4,4-dimethyl-3,5-dioxa-8-azatricyclo[5.2.1.0$^{2,6}$]decan-9-one, approx. 60% based on (1SR,4SR,5RS,6SR)-2-acetyl-5,6-dihydroxy-2-azabicyclo[2.2.1]heptan-3-one, $^1$H-NMR (CDCl$_3$) consistent.

Example 10

(1RS,2SR,3RS,4RS)-N-[2,3-Isopropylidenedioxy-4-(hydroxymethyl)cyclopentan-1-yl]acetamide (formula Va=formula V with R$^2$=R$^3$=methyl)

A solution of 17.7 g (79 mmol) of (1SR,2RS,6SR,7RS)-8-acetyl-4,4-dimethyl-3,5-dioxa-8-azatricyclo[5.2.1.0$^{2,6}$]-decan-9-one in 250 ml of methanol was cooled under an N$_2$ atmosphere to about 0° C. 6.6 g (175 mmol) of sodium borohydride were added in portions over the course of 1 hour so that the temperature was kept below 5° C. The reaction mixture was stirred at room temperature overnight, mixed with a solution of 17.5 g of acetic acid in 20 ml of methanol and brought to dryness in vacuo at 30 to 35° C. The residue was taken up in 100 ml of ethyl acetate, and the white suspension was stirred for 10 minutes and then filtered. The residue on the filter was washed with ethyl acetate (2×20 ml). The combined filtrates were evaporated to dryness and then dried under high vacuum. (Yield: 21.3 g of crude product as viscous yellow oil). 15.0 g of the crude product were chromatographed on silica gel 60 with ethyl acetate/methanol (5:1, v:v).

Yield: 18 g of (1RS,2SR,3RS,4RS)-N-[2,3-isopropylidenedioxy-4-(hydroxymethyl)cyclopentan-1-yl]acetamide (79 mmol) as viscous yellow oil, approx. 100% based on (1SR,2RS,6SR,7RS)-8-acetyl-4,4-dimethyl-3,5-dioxa-8-azatricyclo[5.2.1.0$^{2,6}$]decan-9-one, $^1$H-NMR (CDCl$_3$) consistent.

Example 11

(1RS,2SR,3RS,4RS)-N-[2,3-Isopropylidenedioxy-4-(methoxymethyl)cyclopentan-1-yl]acetamide (formula VIa=formula VI with R$^1$=R$^2$=R$^3$=methyl)

11.5 g (50 mmol) of (1RS,2SR,3RS,4RS)-N-[2,3-isopropylidenedioxy-4-(hydroxymethyl)cyclopentan-1-yl]acetamide in 150 ml of acetone and 2.1 g of 40% strength sodium hydroxide solution were heated to about 50° C. Over the course of 90 minutes, 7.7 g (61 mmol) of dimethyl sulfate and 9.9 g of 40% strength sodium hydroxide solution were metered at 50° C. in parallel. The reaction mixture was stirred further at 50° C. for 3.5 hours and then concentrated to about 30 ml in vacuo. After cooling to about 20° C., 20 ml of water and 40 ml of MTBE were added. The phases were separated and the aqueous phase was extracted with MTBE (2×25 ml).

Evaporation of the combined organic phases to dryness afforded 11.5 g of crude product.

Yield: 11.5 g (47 mmol) of (1RS,2SR,3RS,4RS)-N-[2,3-isopropylidenedioxy-4-(methoxymethyl)cyclopentan-1-yl]-acetamide as red-brown oil (approx. 94% based on (1RS, 2SR,3RS, 4RS)-N-[2,3-isopropylidenedioxy-4-(hydroxymethyl)cyclopentan-1-yl]acetamide), $^1$H-NMR (CDCl$_3$) consistent.

Example 12

Prepurification: extraction of (−)-2-acetyl-2-azabicyclo[2.2.1]hept-5-en-3-one (formula II)

30 l of water were introduced into a 630 l stirring apparatus (enameled steel), and 8.35 kg of hydrochloric acid (technical, 32% strength) were added. Then 3.7 kg of sodium chloride and 150 kg of (−)-2-acetyl-2-azabicyclo[2.2.1]hept-5-en-3-one (89% pure) were put into the reactor. The mixture was stirred gently (experience has shown that an emulsion may form if the stirring speed is too great) at room temperature. After 30 minutes, the stirrer was switched off, and after a further 30 minutes the phases were very readily separable. The resulting, purified (−)-2-acetyl-2-azabicyclo[2.2.1]hept-5-en-3-one was employed immediately after the extraction for preparing (1R,4S,5R,6S)-2-acetyl-5,6-dihydroxy-2-azabicyclo[2.2.1]heptan-3-one.

Yield: about 133 kg of (−)-2-acetyl-2-azabicyclo-[2.2.1]hept-5-en-3-one (approx. 100%, $^1$H-NMR (CDCl$_3$) consistent.

Example 13

(1R,4S,5R,6S)-2-Acetyl-5,6-dihydroxy-2-azabicyclo[2.2.1]heptan-3-one (formula III)

250 kg of aqueous N-4-methylmorpholine N-4-oxide solution (50% strength), 132 l of water and 68 kg of tert-butanol were introduced into a 2500 l stirring apparatus (stainless steel) and then 830 l of acetone were added. 20 kg of 4% strength aqueous osmium tetraoxide solution were added to this mixture at room temperature. Then 150 kg of (−)-2-acetyl-2-azabicyclo[2.2.1]hept-5-ene-3-one were metered in over the course of 1 hour in such a way that the vessel temperature did not exceed 30 to 35° C., and stirring was continued for 1 hour. With a remaining (−)-2-acetyl-2-azabicyclo[2.2.1]hept-5-en-3-one content of less than 0.2%, 58 kg of aqueous sodium bisulfite solution (40% strength) were added at 10 to 50° C. over the course of 1 hour. The reaction solution was then adjusted at a temperature of 10 to 18° C. to pH=5 with sulfuric acid (20% strength).

The residue was centrifuged and washed with acetone (2×20 l). The mother liquor and washings were combined and concentrated by distilling out acetone, tert-butanol and water at 200 to 300 mbar and a temperature below 45° C. The reaction mixture was cooled to 20° C. and adjusted to pH=2 at 12 to 20° C. with sulfuric acid (20% strength). It was then extracted with ethyl acetate (4×670 l), and the combined organic phases were concentrated at 30 to 200 mbar and a temperature below 45° C. The distillation was stopped after the internal temperature rose above 45° C. under 30 to 50 mbar, and the residue was mixed with 620 l of methanol. Ethyl acetate and methanol were distilled out at 200 mbar and an internal temperature of 30° C. until the total amount was 400 l. The reaction solution was cooled to room temperature and then employed directly in the next stage for preparing [1S,2R,6S,7R]-8-acetyl-4,4-dimethyl-3,5-dioxa-8-azatricyclo[5.2.1.0$^{2,6}$]decan-9-one.

Yield about 59% of (1R,4S,5R,6S)-2-acetyl-5,6-dihydroxy-2-azabicyclo[2.2.1]heptan-3-one, $^1$H-NMR (CDCl$_3$) consistent.

Example 14

(1S,2R,6S,7R)-8-Acetyl-4,4-dimethyl-3,5-dioxa-8-azatricyclo[5.2.1.0$^{2,6}$]decan-9-one (formula IVa=formula IV with R$^2$=R$^3$=methyl)

21 kg of toluene-4-sulfonic acid monohydrate were introduced into a 2500 l stirring apparatus (stainless steel) and, at room temperature, 1240 kg of (1R,4S,5R,6S)-2-acetyl-5,6-dihydroxy-2-azabicyclo[2.2.1]heptan-3-one solution (approx. 19% strength) and 250 kg of 2,2-dimethoxypropane were added. The reaction solution was heated at 50° C. for 1 hour and then cooled to 35° C., and 1200 l of methanol were added. After the methanol addition, the content of (1S,2R,6S,7R)-8-acetyl-4,4-dimethyl-3,5-dioxa-8-azatricyclo[5.2.1.0$^{2,6}$]decan-9-one was determined, and the solution was discharged into containers and diluted with methanol for the preparation of (1R,2S,3R,4R)-N-[2,3-isopropylidenedioxy-4-(hydroxymethyl)cyclopentan-1-yl]acetamide.

Yield: 195 kg of (1S,2R,6S,7R)-8-acetyl-4,4-dimethyl-3,5-dioxa-8-azatricyclo[5.2.1.0$^{2,6}$]decan-9-one (approx. 68% based on (1R,4S,5R,6S)-2-acetyl-5,6-dihydroxy-2-azabicyclo[2.2.1]heptan-3-one, $^1$H-NMR (CDCl$_3$) consistent.

Example 15

(1R,2S,3R,4R)-N-[2,3-Isopropylidenedioxy-4-(hydroxymethyl)cyclopentan-1-yl]acetamide (formula Va=formula V with R$^2$=R$^3$=methyl), not isolated 1323 kg of a solution of (1S,2R,6S,7R)-8-acetyl-4,4-dimethyl-3,5-dioxa-8-azatricyclo[5.2.1.0$^{2,6}$]decan-9-one in methanol (approx. 5.3%) were introduced into a 2500 l stirring apparatus (stainless steel) and cooled to about 5° C. 46 kg of sodium borohydride were added over the course of about 4 hours in 12 portions of 3 to 5 kg in such a way that an internal temperature in the stirring apparatus of 10° C. was not exceeded. After the addition was complete, the reaction mixture was warmed to about 20° C. and stirred for 1 hour, and then 53 l of NaOH (30% strength) were added. The methanol was repeatedly distilled out in vacuo and deionized water was added correspondingly to the still. 780 l of acetone were then added to the aqueous solution. After removal of the aqueous phase, the solution of (1R,2S,3R,4R)-N-[2,3-isopropylidenedioxy-4-(hydroxymethyl)cyclopentan-1-yl]acetamide was used further—without isolation directly for preparing (1R,2S,3R,4R)-N-[2,3-isopropylidenedioxy-4-(methoxymethyl)cyclopentan-1-yl]acetamide.

Example 16

(1R,2S,3R,4R)-N-[2,3-Isopropylidenedioxy-4-(methoxymethyl)cyclopentan-1-yl]acetamide (formula VIa=formula VI with R$^1$=R$^2$=R$^3$=methyl), not isolated 70 kg of sodium hydroxide were added to 484 kg of (1R,2S,3R,4R)-N-[2,3-isopropylidenedioxy-4-(hydroxymethyl)cyclopentan-1-yl]acetamide solution in acetone (approx. 15% strength), and the mixture was stirred at 25° C. for 30 minutes. After a time of 30 minutes for phase settlement, the aqueous phase was removed. After addition of a further 30 kg of 30% strength sodium hydroxide solution, the mixture was heated to 50° C. Then, over the course of 75 minutes, 123 kg of dimethyl sulfate (DMS) and 30% strength sodium hydroxide solution were metered in at an internal temperature of 50° C. in parallel so that a pH of from 11 to 13 was maintained. The reaction solution was subsequently stirred for 15 minutes and then cooled to room temperature. After a time of 30 minutes for phase settlement, the aqueous phase was removed. The acetone was distilled out in vacuo until the amount remaining was 500 l, and the (1R,2S,3R,4R)-N-[2,3-isopropylidenedioxy-4-(methoxymethyl)cyclopentan-1-yl]-acetamide solution was cooled to 25° C. and directly reacted further to give (1R,2S,3R,4R)-2,3-isopropylidenedioxy-4-(methoxymethyl)cyclopentan-1-amine.

The yield was not determined and the solution was used directly for preparing (1R,2S,3R,4R)-2,3-isopropylidenedioxy-4-(methoxymethyl)cyclopentan-1-amine. $^1$H-NMR (CDCl$_3$) consistent.

Example 17

(1R,2S,3R,4R)-2,3-Isopropylidenedioxy-4-(methoxymethyl)cyclopentan-1-amine (formula Ia=formula I with R$^1$=R$^2$=R$^3$=methyl)

460 kg of (1R,2S,3R,4R)-N-[2,3-isopropylidenedioxy-4-(methoxymethyl)cyclopentan-1-yl]acetamide solution in acetone (approx. 13.6% strength) were introduced into a 630 l stirring apparatus (stainless steel). The acetone was distilled out at 30 to 300 mbar and a temperature below 45° C. until the acetone content fell below 0.1%, and 400 l of ethanol were added to the reaction mixture. Then, at room temperature, 126 kg of sodium hydroxide solution (50% strength) were added, and the hydrolysis was carried out at about 100° C. and 2 bar over the course of 8 hours. The reaction solution was cooled to room temperature, and ethanol was distilled out at 100 mbar and a temperature of below 45° C. The residue was mixed with 180 l of water, and the remaining amount of ethanol was distilled out. Present in the reactor after the distillation were about 270 l of reaction mixture, which was mixed with 140 l of water and then extracted with MTBE (2×145 l). The combined organic phases were employed directly for preparing (1R,2S,3R,4R)-2,3-isopropylidenedioxy-4-(methoxymethyl)cyclopentan-1-amine hydrogen oxalate. The conversion of (1R,2S,3R,4R)-N-[2,3-isopropylidenedioxy-4-(methoxymethyl)cyclopentan-1-yl]acetamide into (1R,2S,3R,4R)-2,3-isopropylidenedioxy-4-(methoxymethyl)cyclopentan-1-amine was >96.5%. $^1$H-NMR (CDCl$_3$) consistent.

Example 18

(1R,2S,3R,4R)-2,3-Isopropylidenedioxy-4-(methoxymethyl)cyclopentan-1-amine hydrogen oxalate (salt of the compound of the formula I with R$^1$=R$^2$=R$^3$=methyl)

The solution of (1S,2S,3R,4R)-2,3-isopropylidenedioxy-4-(methoxymethyl)cyclopentan-1-amine described in Example 5 was metered over the course of 30 minutes into 23.3 kg of oxalic acid and 210 l of ethanol in a 630 l stirring apparatus (enameled steel). After 60% had been added, the solution was seeded by adding a little (1R,2S,3R,4R)-2,3-isopropylidenedioxy-4-(methoxymethyl)cyclopentan-1-amine hydrogen oxalate. The product which separated out was removed by centrifugation and washed with MTBE/ethanol (60:40) (2×120 l).

Yield: 56 kg of (1R,2S,3R,4R)-2,3-isopropylidenedioxy-4-(methoxymethyl)cyclopentan-1-amine hydrogen oxalate (approx. 78% based on (1R,2S,3R,4R)-N-[2,3-isopropylidenedioxy-4-(methoxymethyl)cyclopentan-1-yl]aceta-mide), $^1$H-NMR (CDCl$_3$) consistent.

The invention claimed is:

1. A method for preparing a compound of formula:

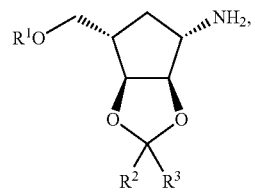

and/or mirror image thereof,
wherein R$^1$ is hydrogen, C$_{1-6}$-alkyl, C$_{3-8}$-cycloalkyl or benzyl, and in which (i) R$^2$ is methyl and R$^3$ is ethyl, or (ii) R$^2$ is hydrogen and R$^3$ is C$_{1-6}$-alkyl or phenyl, or (iii) R$^2$ is methyl and R$^3$ is methyl, or (iv) R$^2$ and R$^3$ together are a group of the formula —(CH$_2$)$_n$— with n=4 to 6, and which is in the form of a free amine or a salt of a dibasic or tribasic organic acid, comprising:

(A) converting a 2-acetyl-2-azabicyclo[2.2.1]hept-5-en-3-one of formula:

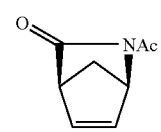

and/or mirror image thereof,
by cis hydroxylation of the double bond into a 2-acetyl-5,6-dihydroxy-2-azabicyclo[2.2.1]heptan-3-one of formula:

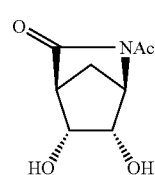

and/or mirror image thereof,
(B) converting the compound of the formula III by reaction with a ketone or an aldehyde of the formula R$^2$—CO—R$^3$, wherein R$^2$ and R$^3$ have the above stated meanings, or by reaction with 2,2-dimethoxypropane or 2,2-dimethoxybutane into a ketal or an acetal of formula:

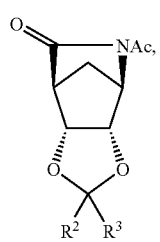

and/or mirror image thereof,
wherein R$^2$ and R$^3$ have the above stated meanings, (C) converting the ketal or acetal of the formula IV by reductive ring opening into a compound of formula:

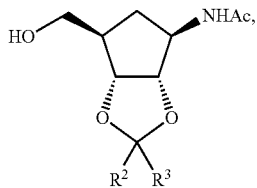

and/or mirror image thereof,
wherein $R^2$ and $R^3$ have the above stated meanings,
(D) optionally converting the compound of formula V or an alcoholate thereof by reaction with dimethyl sulfate, benzyl chloride or a halide of the formula $R^1$—X wherein $R^1$ has the above stated meaning other than hydrogen, and X is bromine or iodine, into an ether of formula:

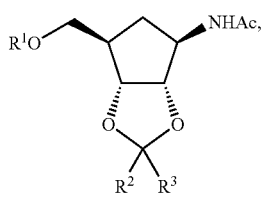

and/or mirror image thereof,
wherein $R^1$ has the above stated meaning other than hydrogen and $R^2$ and $R^3$ have the above stated meanings,
(E) converting a compound of the formula V or VI by alkaline hydrolysis into a compound of formula:

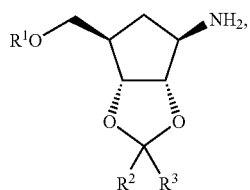

and/or mirror image thereof,
wherein $R^1$, $R^2$ and $R^3$ have the above stated meanings, and
(F) optionally converting the compound of the formula I by addition of a dibasic or tribasic organic acid into corresponding salt wherein $R^1$, $R^2$ and $R^3$ have the above stated meanings.

2. The method as claimed in claim 1, wherein the cis hydroxylation of the double bond is carried out using osmium tetraoxide.

3. The method as claimed in claim 2, wherein the osmium tetraoxide is used in an amount of from 0.1 to 2.0 mol percent based on the compound of the formula II, and the compound of the formula II is regenerated during the reaction.

4. The method as claimed in claim 3, wherein the osmium tetraoxide is regenerated by adding a sterically demanding N-oxide or a mixture of a sterically demanding amine with hydrogen peroxide.

5. The method as claimed in claim 4, wherein the formation of the ketal or acetal of formula IV is carried out with acid catalysis.

6. The method as claimed in claim 5, wherein sulfuric acid and/or p-toluenesulfonic acid is used for the acid catalysis.

7. The method as claimed in claim 6, wherein acetone or 2,2-dimethoxypropane is employed for forming the ketal or acetal.

8. The method as claimed in claim 7, wherein the reductive ring opening is carried out with a complex metal hydride.

9. The method as claimed in claim 8, wherein an alcohol of the formula V is converted with dimethyl sulfate into the methyl ether.

10. The method as claimed in claim 8, wherein an alcohol of the formula V is converted with methyl iodide into the methyl ether.

11. The method as claimed in claim 10, wherein the alkaline hydrolysis is carried out with at least one alkali metal or alkaline earth metal hydroxide selected from the group consisting of LiOH, NaOH, KOH, Ca(OH)$_2$, and Ba(OH)$_2$, in aqueous and/or alcoholic solution or suspension.

12. The method as claimed in claim 11, wherein the alkaline hydrolysis is carried out under a pressure of from 1 to 10 bar, and at a temperature of from 50 to 150° C.

13. The method as claimed in claim 12, wherein the organic acid is selected from the group consisting of oxalic acid free of water of crystallization and/or containing water of crystallization, (+)-, (−)- or meso-tartaric acid, (+)- or (−)-malic acid, tartronic acid, mesoxalic acid and oxaloacetic acid.

14. The method as claimed in claim 13, wherein oxalic acid free of water of crystallization and/or containing water of crystallization is employed as organic acid for the salt formation.

15. A compound of formula:

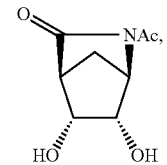

or mirror image thereof.

16. A compound of formula:

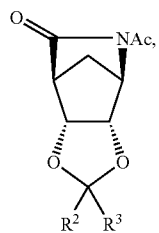

or mirror image thereof,
wherein $R^1$ is hydrogen, $C_{1-6}$-alkyl, $C_{3-8}$-cycloalkyl or benzyl, and (i) $R^2$ is methyl and $R^3$ is ethyl, or (ii) $R^2$ is hydrogen and $R^3$ is $C_{1-6}$-alkyl or phenyl, or (iii) $R^2$ is methyl and $R^3$ is methyl, or (iv) $R^2$ and $R^3$ together are a group of the formula —(CH$_2$)$_n$— with n=4 to 6.

17. A compound of formula:

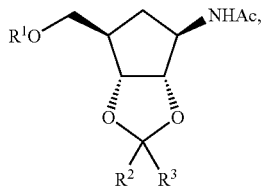

or mirror image thereof,
wherein $R^1$ is $C_{1-6}$-alkyl, $C_{3-8}$-cycloalkyl or benzyl, and (i) $R^2$ is methyl and $R^3$ is ethyl, or (ii) $R^2$ is hydrogen and $R^3$ is $C_{1-6}$-alkyl or phenyl, or (iii) $R^2$ is methyl and $R^3$ is methyl, or (iv) $R^2$ and $R^3$ together are a group of the formula —$(CH_2)_n$— with n=4 to 6.

18. The method as claimed in claim 2, wherein the osmium tetraoxide is used in an amount of from 0.1 to 2.0 mol percent, based on the compound of the formula II, and the compound of the formula II is regenerated during the reaction.

19. The method as claimed in claim 1, wherein the formation of the ketal or acetal of formula IV is carried out with acid catalysis.

20. The method as claimed in claim 19, wherein sulfuric acid and/or p-toluenesulfonic acid is used for the acid catalysis.

21. The method as claimed in claim 6, wherein acetone or 2,2-dimethoxypropane is employed for forming the ketal or acetal.

22. The method as claimed in claim 8, wherein the complex metal hydride is $NaBH_4$.

23. The method as claimed in claim 1, wherein the reductive ring opening is carried out with a complex metal hydride.

24. The method as claimed in claim 23, wherein the complex metal hydride is $NaBH_4$.

25. The method as claimed in claim 1, wherein an alcohol of the formula V is converted with dimethyl sulfate into the methyl ether.

26. The method as claimed in claim 1, wherein an alcohol of the formula V is converted with methyl iodide into the methyl ether.

27. The method as claimed in claim 1, wherein the alkaline hydrolysis is carried out with at least one alkali metal or alkaline earth metal hydroxide selected from the group consisting of LiOH, NaOH, KOH, $Ca(OH)_2$, and $Ba(OH)_2$, in aqueous and/or alcoholic solution or suspension.

28. The method as claimed in claim 12, wherein the alkaline hydrolysis is carried out under a pressure of from 1 to 2 bar, and at a temperature of from 80 to 100° C.

29. The method as claimed in claim 1, wherein the alkaline hydrolysis is carried out under a pressure of from 1 to 10 bar, and at a temperature of from 50 to 150° C.

30. The method as claimed in claim 29, wherein the alkaline hydrolysis is carried out under a pressure of from 1 to 2 bar, and at a temperature of from 80 to 100° C.

31. The method as claimed in claim 1, wherein the organic acid is selected from the group consisting of oxalic acid free of water of crystallization and/or containing water of crystallization, (+)-, or (−)- or meso-tartaric acid, (+)- or (−)-malic acid, tartronic acid, mesoxalic acid and oxaloacetic acid.

32. The method as claimed in claim 31, wherein oxalic acid free of water of crystallization and/or containing water of crystallization is employed as organic acid fro the salt formation.

* * * * *